United States Patent [19]

Millsap

[11] 4,162,764

[45] Jul. 31, 1979

[54] PERSONNEL AIR COOLING DEVICE

[76] Inventor: Robert K. Millsap, 500 E. 1st, Pana, Ill. 62557

[21] Appl. No.: 843,435

[22] Filed: Oct. 18, 1977

[51] Int. Cl.² .............................................. B05B 9/08
[52] U.S. Cl. ........................................ 239/152; 98/1; 128/400
[58] Field of Search ..................... 98/1 R, 50; 165/46; 62/259; 128/400, 402, 379, 256; 239/152-154

[56] References Cited

U.S. PATENT DOCUMENTS

| | | | |
|---|---|---|---|
| 2,255,751 | 9/1941 | Bancel | 98/1 |
| 2,540,547 | 2/1951 | Rodert | 165/46 X |
| 3,075,517 | 1/1963 | Morehead | 128/400 |
| 3,223,172 | 12/1965 | Moss | 239/152 X |
| 3,523,645 | 8/1970 | Beauchamp | 239/154 |
| 3,610,323 | 10/1971 | Troyer | 165/46 |

*Primary Examiner*—John H. Love
*Attorney, Agent, or Firm*—Cohn, Powell & Hind

[57] ABSTRACT

This air cooling device includes a waist belt worn under the clothing of the wearer and having an apertured, waist-encircling air tube attached thereto. The air tube is connected to an air supply by means of an extension air line having an air pressure reducing regulator valve at one end. The device also includes an apertured neck-encircling air tube attached to the waist-encircling air tube. The ends of the waist tube are separable to facilitate removal from the wearer with the waist belt.

3 Claims, 5 Drawing Figures

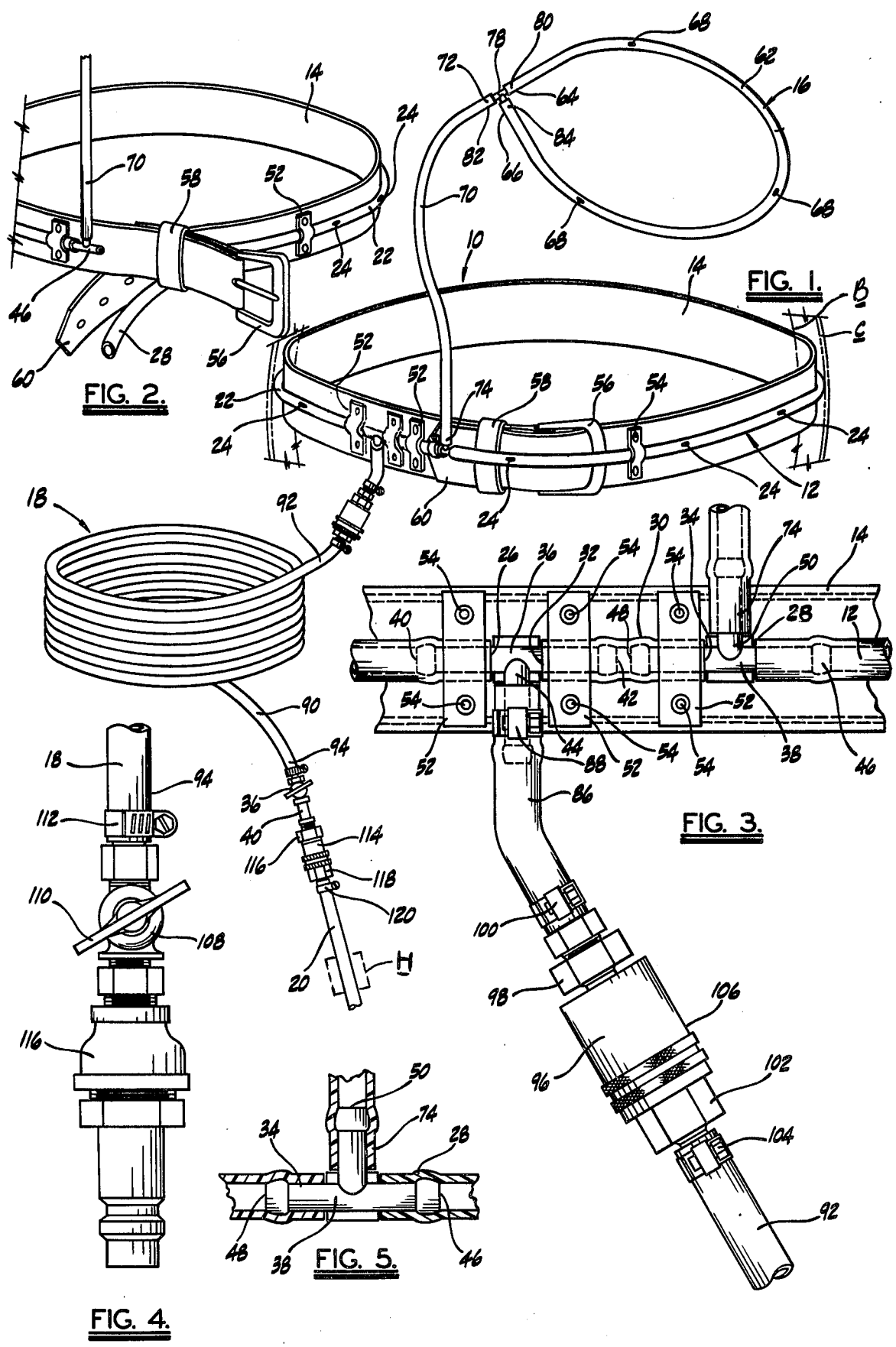

PERSONNEL AIR COOLING DEVICE

BACKGROUND OF THE INVENTION

This invention relates generally to an air cooling device for increasing the comfort of operators under high temperature conditions, and particularly to a device which is connectable to a main line high pressure air supply.

There are many instances in which personnel, such as welders and other craftsmen, are exposed to a high temperature environment which reduces their efficiency because of the discomfort suffered. Welders working in the field on extremely hot days and in close proximity to sun-exposed metal structures, without shade, provide one example of a situation in which the heat can be so intense as to permit work to be carried out only for short periods of time and even then in considerable discomfort. Automobile assembly line operators provide another example of craftsmen who suffer from summer heat because of the impracticality of air conditioning large plant buildings. Long distance truck drivers provide a third example of personnel who suffer discomfort from summer heat because in many instances the truck cabs are not air conditioned. In all of these environmental situations a relatively inexpensive air supply is available in the form of high pressure outlets which are used to supply air to pneumatic equipment and for other purposes.

The prior art discloses several instances of air conditioning systems built directly into clothing for special purposes. However, none of the known systems provides a device of the character of the present device which is used with a high pressure air supply and is suitable for such a wide range of uses.

SUMMARY OF THE INVENTION

This air cooling device provides a means of supplying individualized air conditioning to personnel working under high temperature conditions.

The air cooling device is used in conjunction with a high pressure outlet and includes a waist belt; an air tube, which includes a waist portion attached to the belt and having a plurality of air emitting apertures and a connection means; an extension air line having one end attached to the waist portion and the other end connected to the high pressure outlet, and a regulator valve at one end of the extension air line for controlling the air pressure supply to the waist portion.

The air tube means includes a looped neck portion operatively attached to the waist portion and having a plurality of air emitting apertures.

The waist portion of the air tube includes spaced end portions and the connection means connects said spaced end portions together to permit the circumferential flow of air through said waist portion.

The waist portion of the air tube includes first and second portions and the connector means includes a pair of tee connectors connecting said first and second portions, one of the tee connectors providing a connection for the extension air line and the other of the connectors providing a connection for the looped neck portion.

The looped neck portion includes a first portion having one end connected to an associated tee connector and a second neck-encircling portion having opposed ends connected to the other end of said first portion by means of an associated tee connector.

The extension air line means includes quick connect-disconnect couplings at each end and the regulator valve means is disposed adjacent one of said couplings. The waist portion connection means includes a short, flexible tube disposed between said waist portion and an associated quick connect-disconnect coupling to avoid strain at the connection point.

The device can be converted into a heating device by preheating the air supply.

This personnel air cooling device is inexpensive to manufacture and operate and provides superior individualized cooling while permitting flexibility of movement to the wearer.

BRIEF DESCRIPTION OF THE DRAWINGS

FIG. 1 is a perspective view of the personnel air cooling device showing the waist belt in a connected position;

FIG. 2 is a fragmentary perspective view similar to FIG. 1 but showing the belt in a disconnected condition;

FIG. 3 is an enlarged view of the end of the extension air line connected to the air tube;

FIG. 4 is an enlarged view showing the regulator valve; and

FIG. 5 is an enlarged fragmentary view illustrating a tee fitting connector.

DESCRIPTION OF THE PREFERRED EMBODIMENT

Referring now by reference numerals to the drawing and first to FIG. 1 it will be understood that the personnel air cooling device is generally indicated by numeral 10 and includes a lower, apertured waist-encircling tubular portion 12 carried by a belt 14; an upper, apertured looped, tubular portion 16 connected to the waist portion 12 and an extension line 18 connected at one end to the waist portion and at the other end to a mainline air supply hose generally indicated by numeral 20. The upper and lower portions 12 and 14 provide air emitting air tube means providing a cooling system for the wearer.

More specifically, as shown in FIGS. 1 and 3, the waist portion 12 includes a flexible tube 22 constituting a first tubular portion having a plurality of circumferentially disposed, upwardly directed apertures 24 disposed between opposed ends 26 and 28. The ends 26 and 28 of the tube 22 are operatively interconnected together by means of a short length of tube 30 constituting a second tubular portion and having ends 32 and 34 and tee connectors 36 and 38 constituting first and second connector means respectively. The connector 36 includes opposed end portions 40 and 42 received within associated tubular ends 26 and 32 respectively, and a stem end portion 44. The connector 38 includes opposed end portions 46 and 48 which are received within associated tubular end portions 28 and 34 respectively, and a stem end portion 50. In the preferred embodiment the flexible tubes 22 and 30 are removably attached to the belt 14 as by a plurality of front clips 52 and a pair of rear clips 52 (not shown) which are attached to the belt as by rivets 54. The belt 14 is provided with a buckle 56 and loop 58 at one end receiving the perforated belt end 60 in the conventional manner.

The looped tubular portion 16 includes a neck-encircling second portion 62 having opposed ends 64 and 66 and a plurality of apertures 68 disposed therebetween and an elongate first portion 70, having opposed ends 72 and 74 and a tee connector 78, constituting a third connector, is provided having end portions 80 and 82 and stem end portion 84 receiving tubular ends 64, 72 and 66 respectively. The other end 74 of the elongate tube 70 is received by the stem end portion 50 of the connector 38. The stem end portion 44 of connector 36 is provided with a relatively short length of flexible tubing 86 which is attached in depending relation to said stem end portion 44, as by a clamp 88.

As best shown in FIGS. 1, 3 and 4, the extension line 18 includes an elongate flexible hose 90 having opposed ends 92 and 94. The hose end 92 is connected to the short flexible tubing 86 as by a conventional quick connect-disconnect coupling 96 having a male portion 98 attached to hose 86 as by clamp 100, and a female portion 102 attached to flexible hose end 92 as by clamp 104, said female portion being provided with a movable locking collar 106. The other end 94 of the flexible hose 90 is provided with a regulator valve 108 having a handle 110, said regulator valve 108 being attached to the hose end 94 by a clamp 112. Another conventional quick connect-disconnect coupling 114 provides a means by which the flexible hose is connected to the mainline air supply hose outlet 20 said coupling 114 having a male portion 116 threadedly attached to the regulator 108 and a female portion 118 connected to the mainline supply hose 20 as by clamp 120.

It is thought that the structural features and structural advantages of this personnel air cooling device have become fully apparent from the foregoing description of parts, but for completeness of disclosure the operation of the device will be briefly described.

The device is intended to be worn under the shirt or other clothing C of the wearer so that, in effect, the clothing acts as a conduit to distribute cooling air to the upper body B of the wearer. The tee connector 38, shown in FIG. 5, is of a size relative to the tube 22 to permit the tube end 28 to be firmly held on the tee end portion 46 and yet be readily pulled from said end portion 46 and easily replaced. This arrangement permits the tube 22 to be disconnected just before the belt is unbuckled, see FIG. 2, and facilitates removal of the device. Alternatively, the tube end 28 can be plugged closed and an angle connector used in lieu of the tee connector 38, in which case the device can be removed simply by unbuckling the belt 14.

It is unnecessary to break the connection of the loop portion 16 for emplacement on the wearer and the provision of the elongate portion 70 permits the neck-embracing portion 62 to be positioned before or after the belt 14 is buckled on. The provision of quick connect-disconnect couplings 92 and 114 at each end of the extension line 18 facilitates the ease of use of the device and the provision of a regulator adjacent the main line air supply end of the line 18 ensures that said extension line is not subject to main line pressure. In the preferred embodiment the main line pressure is commonly 100 psi such as is found in many factory outlets. This results in a controlled pressure of 40 psi entering the waist tube 22 and this pressure can be readily controlled by the regulator valve 108 to provide maximum pressure in the apertured tubular portions which is further reduced to about 10 psi body contact pressure to provide adequate air cooling for most purposes.

As will be readily understood, the extension air line permits the wearer considerable freedom of movement particularly in view of the connections used. The short length of imperforate flexible tube 86 extending between the quick connect-disconnect coupling 96 and the tee connector 36 provides the connection with a degree of flexibility, as opposed to the relative rigidity of a direct connection between the tubular portion 12 and the coupling 96. This flexibility reduces the chances of an air pressure break in the connection at this point. In addition, it will be understood that the disposition of the regulator provides for reduced pressure at the upper end of the extension air line and it would be possible, by providing a suitable sizing of parts, to omit the clamp 88 attaching the flexible tube 86 to the tee connector 36 so that the connect-disconnect can be made at this point.

This device when used in conjunction with a high pressure outlet as described provides a cooling system. However, it will be understood that the device can readily be adapted to supply heated air by heating the air supply before it is passed from the main line air supply 18 into the hose 20, as by utilizing a heater unit indicated by H.

I claim as my invention:

1. A personnel temperature control device for use with a high pressure outlet, the device comprising:
   (a) waist belt means,
   (b) elongate air tube means, including:
      1. connection means connected to the waist belt means,
      2. a neck-encircling loop portion adapted to hang freely about the neck, and
      3. a portion connected between the neck-encircling portion and the connection means,
      4. at least the neck-encircling loop portion including a plurality of longitudinally spaced air outlet apertures for expelling air outwardly in a direction transverse to the longitudinal axis of the air tube means onto the upper body of the wearer.
   (c) an extension air line means including opposed ends, one of said ends being connected to said connection means, and the other end being connected to the high pressure outlet, and
   (d) regulator valve means at one end of the extension air line means for controlling air pressure supply to air tube means.

2. A device as defined in claim 1, in which:
   (e) said neck encircling loop portion includes opposed ends, and
   (f) said air tube means includes a tee connector having three arm portions, two of said arm portions connecting said opposed ends and the other of said arm portions connecting said neck encircling portion to said other portion.

3. A device as defined in claim 1, in which:
   (g) both portions of said air tube means are single strand tubes.

* * * * *